(12) United States Patent
Kwon et al.

(10) Patent No.: US 6,220,861 B1
(45) Date of Patent: Apr. 24, 2001

(54) OSSEO-INTEGRATED DENTAL IMPLANT

(76) Inventors: Jong Jin Kwon, 35-47 Jongkok-dong, Kwangjin-ku; Young Keun Hyun, 10-303, Wooseong Apt., Jeonnong-dong, Dongdaemon-ku, both of Seoul (KR)

( * ) Notice: Subject to any disclaimer, the term of this patent is extended or adjusted under 35 U.S.C. 154(b) by 0 days.

(21) Appl. No.: 09/386,318

(22) Filed: Aug. 31, 1999

(30) Foreign Application Priority Data

Jul. 7, 1999 (KR) .................................................. 99-27318

(51) Int. Cl.[7] ...................................................... A61C 8/00

(52) U.S. Cl. .......................................... 433/173; 433/174

(58) Field of Search .................................. 433/173, 174, 433/201.1

(56) References Cited

U.S. PATENT DOCUMENTS 5,316,476 * 5/1994 Krauser ................................. 433/173
5,324,199 * 6/1994 Branemark ....................... 433/173 X

* cited by examiner

Primary Examiner—Nicholas D. Lucchesi
(74) Attorney, Agent, or Firm—Staas & Halsey LLP

(57) ABSTRACT

An osseo-integrated dental implant comprising a band is disclosed. The band is spaced apart from an upper end of a root of the implant at a predetermined distance and which is highly polished in a circumferential direction. Preferably, the band is concavely formed and is located between one-third position and two-third position of overall length of the root from the upper end of the root of the implant. When there is a failure of treatment caused by loss of surrounding bone of cervical portion of the implant, the implant with peri-implantitis in progress can be easily treated and then the longevity of the implant can be lengthened.

10 Claims, 7 Drawing Sheets

OSSEO-INTEGRATED DENTAL IMPLANT

FIELD OF THE INVENTION

The present invention relates to an osseo-integrated dental implant, and more particularly, to an osseo-integrated dental implant having a highly polished band thereon.

BACKGROUND OF THE INVENTION

The osseo-integrated dental implant (hereinafter referred to as "implant") is also called an endosseous implant. The clinical application of the implant is on the rapid increase because of high clinical success rate and excellent function of the implant. The implants are divided into various types, for example, an endosteal implant, a subperiosteal implant and a transosteal implant, etc. Among the various types of the implants, the endosteal implant is widely used. The endosteal implant is made of chrome-cobalt, ceramic, titanium, etc. as materials, and involves a screw type as shown in FIG. 1A and a cylinder type as shown in FIG. 1B and hybrid type of screw and cylinder. These implants are independently implanted or are connected with natural tooth.

In recent years, much research and many developments of the implant have been continuously done as important tasks in dental science. However, all the research and development of the implants are focused on an increase of a contact surface between the implant and the bone, and the research in long term evaluation of the surrounding bone of the implant has been scarcely performed. Even in the clinically successful implants, since the osseeointegration is imperfect or the bone defect is generated at the cervical portion of the implants, failures of the implants frequently happen. Therefore, many sufferers will complain of pain due to disease of the surroundings of the implants.

The failures of the implants are caused by repeated microfracture of the bone due to overload to the implants or bacterial infection of the surrounding bone of the implants, etc. However, all the implants pass through peri-implantitis regardless of causes of the failures. This peri-implantitis gives rise to inflammation of mucosa, loss of attached gingiva, exposure of a cervical portion of the implant and loss of the surrounding bone, etc. Therefore, the peri-implantitis has to be properly treated at an initial stage to maintain functions of the implant. FIG. 2A illustrates the peri-implantitis in progress in surroundings of implant and this state requires treatment of the implant and surrounding tissue.

Conventionally, the periosurgery is performed in the surroundings of the implant and the toxin, which is formed in the root portion of the infected implantis, is removed in order to treat the peri-implantitis at the initial stage. Also, the surface of the screw of the implant shown in FIG. 2B or the unevenness of a plasma surface or coated surface by hydroxypatite is removed and then the surface is highly polished.

However, the implant according to the prior art has a disadvantage in that it is very difficult to accurately polish the infected surface of a subgingival area in a root portion of the implant by a curette for dental implant or a dental high speed burr for treatment of the peri-implantitis. Also, the implant according to the prior arts has a problem in that a bone defect and inflammation may be rapidly and downwardly spread due to rough surface characteristics when bone damage occurs at a cervical portion of the implant.

SUMMARY OF THE INVENTION

It is an object of the present invention to provide a new and improved osseo-integrated dental implant wherein the implant with peri-implantitis in progress can be easily treated and then the longevity of the implant can be lengthened.

It is another object of the present invention to provide a new and improved osseo-integrated dental implant preventing a bone defect and inflammation at a surface of the implant from being downwardly spread.

It is further object of the present invention to provide a new and improved osseo-integrated dental implant serving as a base for a polishing exposure surface of root of the infected implant with a bone defect in progress.

According to the present invention, these and other objects and advantages are by providing an osseo-integrated dental implant comprising a band which is spaced apart from an upper end of a root of the implant at a predetermined distance and which is polished in a circumferential direction.

The various features of novelty which characterize the invention are pointed out with particularity in the claims annexed to and forming a part of this disclosure.

For a better understanding of the invention, its operating advantages and specific objects attained by its uses, reference is made to the accompanying drawings and descriptive matter in which the preferred embodiments of the invention are illustrated.

BRIEF DESCRIPTION OF THE DRAWINGS

These and other objects and advantages of the invention will become apparent and more readily appreciated from the following description of the preferred embodiments, taken in conjunction with the accompanying drawings of which.

DETAILED DESCRIPTION OF THE PREFERRED EMBODIMENTS

This invention will be described in further detail by way of embodiments with reference to the accompanying drawings.

Figure 1A:
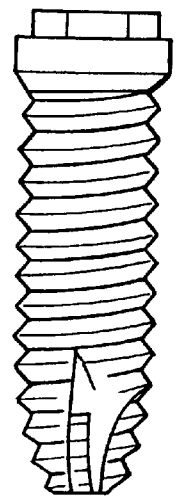
FIG. 1A is a front view illustrating a screw type of implant according to the prior art.
Figure 1B:
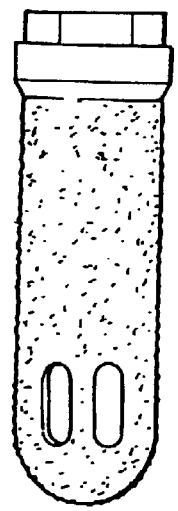
FIG. 1B is a front view illustrating a cylinder type of implant according to the prior art.
Figure 2A:
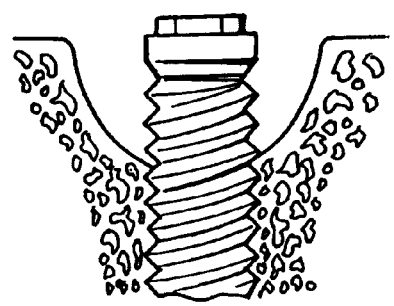
FIG. 2A is a fragmentary sectional view of the screw type of implant according to the prior art illustrating a state that the cervical area of surrounding bone of the implant is destroyed.
Figure 2B:
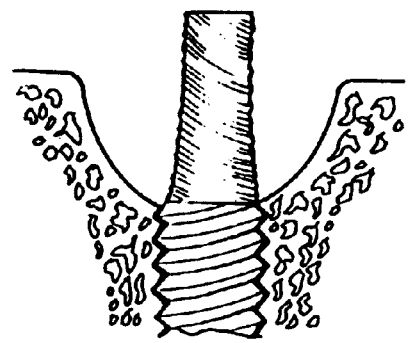
FIG. 2B is a fragmentary sectional view of the screw of an implant wherein a polishing method is clinically applied to the implant.
Figure 3A:
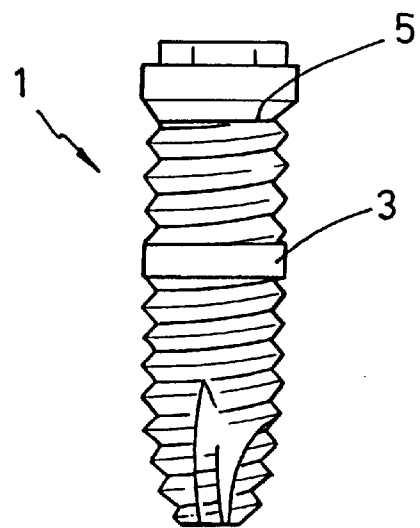
FIG. 3A to FIG. 3E are front views of embodiments of a screw type of implant according to the present invention.
Figure 3B:
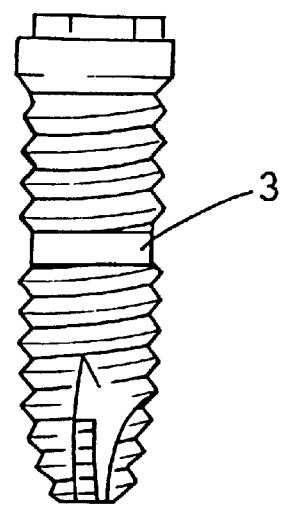
Figure 3C:
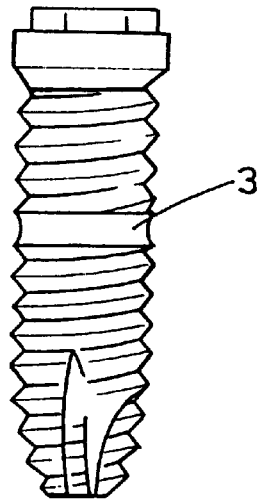
Figure 3D:
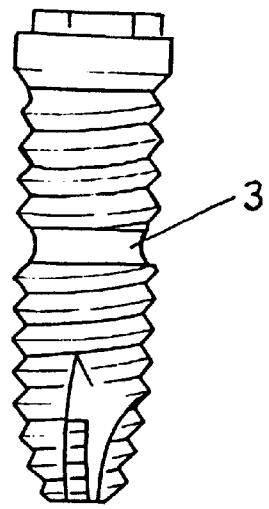
Figure 3E:
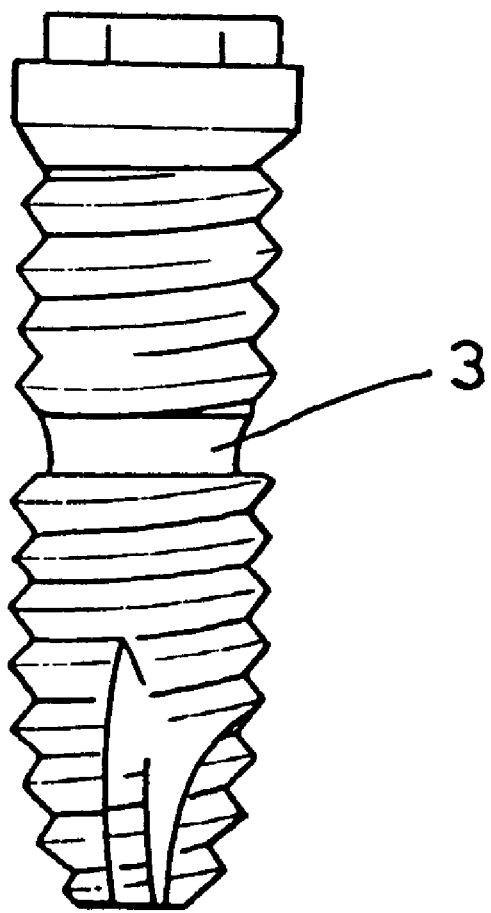
Figure 4A:
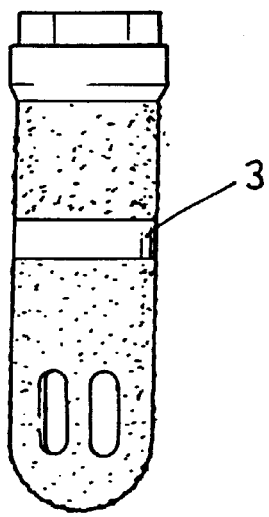
FIG. 4A to FIG. 4C are front views of embodiments of a cylinder type of implant according to the present invention.
Figure 4B:
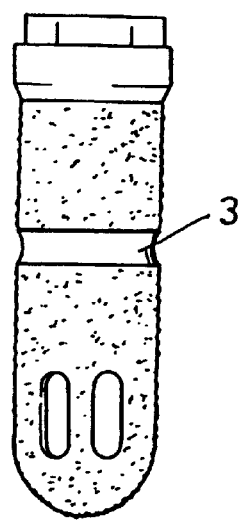
Figure 4C:
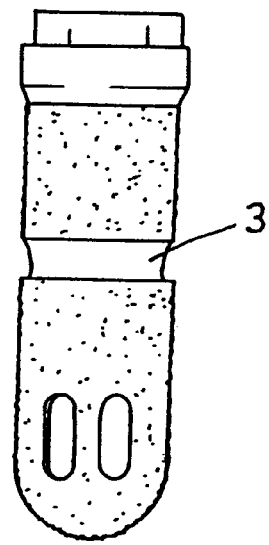

Referring to FIG. 3A to FIG. 4C, an implant according to the present comprises a highly polished band 3 as a main feature which is located at a predetermined position of a root 1. The band 3 has a surface roughness below substantially 0.5 $\mu$m. The machined-prepared surface of the band 3 is flat as shown in FIG. 3A, FIG. 3B, and FIG. 4A and, preferably, is concavely formed as shown in FIG. 3C, FIG. 3D, and FIG. 4B. The concave band in comparison with the flat band can be easily sensed by X-ray examination. Therefore, whether or not a bone defect has spread to the position of the band 3 can be easily observed by the concave band. Also, the concave band has a larger contact area than the flat band. On the other hand, the band can have a trumpet shape with a diameter which becomes smaller from an upper portion to a lower portion as shown in FIG. 3E and FIG. 4C. Also, the surface of the band 3 can be aligned with extension lines of screw ridges as shown in FIG. 3A, and the surface of the band 3 can be aligned with extension lines of screw valleys as shown in FIG. 3B.

According to the present invention, dentists can easily operate dental high speed burrs when a polishing method is applied to an upper portion of the band 3 by forming the polished band. The implant treatment is generally evaluated as a failure when the degree of bone loss exceeds one-third in comparison with an initially implanted length of the implant regardless of overall length of the implant. Therefore, the implant according to the prior art is maintained by conventional methods when the degree of bone loss is below one-third of the implanted length of the implant, and treatment of dental implant accompanying a polishing of an infected area is applied to the implant to lengthen longevity of the implant when the degree of bone loss is above one-third of the implanted length of the implant. Accordingly, preferably, the band 3 is located between a one-third position and a two-third position position of overall length of the root 1 from an upper end 5 of the root 1.

The band 3 has various widths in accordance with overall length of the implant, a patient's hygiene, a position of the implant and bone quality, etc. The band 3 is 0.5 mm to 1.0 mm in width when the overall length of the root 1 is below 8 mm, and is 0.5 mm to 1.2 mm in width when the overall length of the root 1 is between 9 mm and 12 mm, and said band 3 is 0.5 mm to 1.5 mm in width when the overall length of the root 1 is above 13 mm.

On the other hand, as shown in FIG. 3A to FIG. 4C, the band 3 can be applied to all the implants which are clinically used at present. The screw type of implant comprises a band formed by removing a part from the screw as shown in FIG. 3A to FIG. 3E, and the cylinder type of implant comprises a band formed by removing a coated surface of the implant to expose pure titanium as shown in FIG. 4A to FIG. 4C.

Figure 5:
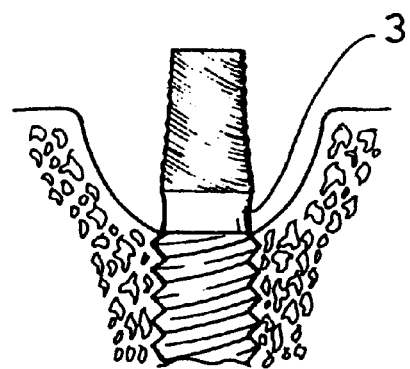
FIG. 5. is a fragmentary sectional view of the screw of an implant according to the present invention wherein a polishing method is clinically applied to the implant.

Referring to FIG. 5, FIG. 5 illustrates an implant wherein the polishing method is clinically applied to an infected surface of the implant. As shown in FIG. 5, when the upper portion of the implant is polished by a dental high speed burr, the band 3 comes into contact with soft tissue at an upper portion of the bone since the band 3 has been already highly polished. Accordingly, a superstructure of the implant can be easily remanufactured.

Analyses by a finite element method have been applied to various specimen models of the implant according to the present invention to analyse stress size and stress distribution of the implant. As an example, the specimen models according to the present invention have 10 mm in length and 0.6 mm, 0.8 mm, and 1.0 mm in width, respectively. The polished band of the specimen models is located at a one-third position of the overall length of the root from the upper end of the root. The specimen models without any band according to the prior art have been prepared to compare with the specimen models with a band according to this invention. A vertical load 100N as a static load has been applied to a midportion of an upper part of the implant models and a horizontal load 25N has been applied. Results an analysis by the finite element method show that a difference of the maximum equivalent stresses generated in the implant is below 0.03% in a screw type of implant and is below 1.4% in a cylinder type of implant, and has no meaningful difference. Accordingly, it can be ascertained that the implant according to the present invention hardly causes a biomechanically difference. Also, experiments on animals have been made. As an example, the implant with the same conditions as mentioned above has been applied to a mandible of a dog. Experimental results show that bone contact of the polished band is very satisfactory.

The invention is in no way limited to the embodiments described hereinabove. Various modifications of disclosed embodiments as well as other embodiments of the invention will become apparent to persons skilled in the art upon reference to the description of the invention. It is therefore contemplate that the appended claims will cover any such modification or embodiments as fall within the true scope of the invention.

What is claimed is:

1. An osseo-integrated dental implant, comprising:
   a root comprising a band located between a one-third and a two-third position of an overall length of said root of the osseo-integrated dental implant as measured from an upper end of the said root, said band being polished in a circumferential direction to have a surface roughness of below 0.5 μm, wherein a width of said band is 0.5 mm to 1.0 mm when the overall length of said root is below 8 mm, and 0.5 mm to 1.2 mm when the overall length of said root is between 9 mm and 12 mm, and 0.5 mm to 1.5 mm when the overall length of said root is above 13 mm.

2. The osseo-integrated dental implant as claimed in claim 1, wherein said band has a trumpet shape, wherein a diameter becomes smaller from an upper portion to a lower portion thereof.

3. The osseo-integrated dental implant as claimed in claim 1, wherein the osseo-integrated dental implant is a screw-type with screw ridges and valleys, wherein said band has ends which are aligned with extension lines of the screw ridges.

4. The osseo-integrated dental implant as claimed in claim 3, wherein an exterior surface of said band in a direction of the width of said band is flat.

5. The osseo-integrated dental implant as claimed in claim 1, wherein the osseo-integrated dental implant is a screw-type with screw ridges and valleys, wherein said band has ends which are aligned with extension lines of the screw valleys.

6. The osseo-integrated dental implant as claimed in claim 5, wherein an exterior surface of said band in a direction of the width of said band is flat.

7. The osseo-integrated dental implant as claimed in claim 1, wherein the osseo-integrated dental implant is a cylinder-type, wherein said band is flush with the remaining exterior surface of the osseo-integrated dental implant.

8. The osseo-integrated dental implant as claimed in claim 1, wherein the osseo-integrated dental implant is a cylinder-type, wherein said band has a trumpet shape, wherein a diameter becomes smaller from an upper portion to a lower portion thereof, and an end of said band is flush with the remaining exterior surface of the osseo-integrated dental implant.

9. The osseo-integrated dental implant as claimed in claim 1, wherein an exterior surface of said band in a direction of the width of said band is flat.

10. The osseo-integrated dental implant as claimed in claim 1, wherein the osseo-integrated dental implant is a cylinder-type, and an exterior surface of said band in a direction of the width of said band is flat.

* * * * *